(12) United States Patent
Emmel et al.

(10) Patent No.: US 7,794,632 B2
(45) Date of Patent: Sep. 14, 2010

(54) PROCESS FOR THE PREPARATION OF PURE ARYLLITHIUM COMPOUNDS AND THEIR USE

(75) Inventors: Ute Emmel, Frankfurt am Main (DE); Wilfried Weiss, Oberursel (DE); Ulrich Wietelmann, Friedrichsdorf (DE); Dirk Dawidowski, Frankfurt (DE)

(73) Assignee: Chemetall GmbH, Frankfurt am Main (DE)

( * ) Notice: Subject to any disclaimer, the term of this patent is extended or adjusted under 35 U.S.C. 154(b) by 0 days.

(21) Appl. No.: 11/725,614

(22) Filed: Mar. 20, 2007

(65) Prior Publication Data

US 2007/0187847 A1 Aug. 16, 2007

Related U.S. Application Data

(63) Continuation of application No. 11/293,343, filed on Dec. 2, 2005, now abandoned, which is a continuation of application No. 10/202,996, filed on Jul. 22, 2002, now abandoned.

(30) Foreign Application Priority Data

Sep. 19, 2001 (DE) .............................. 101 46 233

(51) Int. Cl.
*C07F 1/02* (2006.01)
(52) U.S. Cl. ................................................. 260/665 R
(58) Field of Classification Search ............. 260/665 R
See application file for complete search history.

(56) References Cited

U.S. PATENT DOCUMENTS 3,446,860 A * 5/1969 Beumel, Jr. ............. 260/665 R
3,780,045 A * 12/1973 Scretta ....................... 546/184

FOREIGN PATENT DOCUMENTS

WO 92/19622 * 11/1992

* cited by examiner

*Primary Examiner*—Shailendra Kumar
(74) *Attorney, Agent, or Firm*—Fulbright & Jaworski L.L.

(57) ABSTRACT

A process is described for preparing aryllithium compounds by reaction of metallic lithium in an ether-containing solvent with an aryl halide, wherein prior to or at the beginning of the reaction a catalyst is added, the catalyst containing a halogen-free, polynuclear aromatic (aryl catalyst) or consisting of such a compound.

18 Claims, No Drawings

PROCESS FOR THE PREPARATION OF PURE ARYLLITHIUM COMPOUNDS AND THEIR USE

This application is a continuation of application Ser. No. 11/293,343 filed Dec. 2, 2005, now abandoned incorporated herein by reference in its entirety, which is a continuation of application Ser. No. 10/202,996 filed Jul. 22, 2002 (now abandoned), which claimed priority from German Patent Application No. 101 46 233.6 filed Sep. 19, 2001.

This invention relates to a process for the preparation of pure aryllithium compounds and their use.

The preparation of aryllithium compounds in organic solvents by reacting aryl halides with lithium metal has been known for a long time. Because aryllithium compounds are usually insoluble in hydrocarbons, preferred organic solvents are ethereal solvents, for example, diethyl ether. However, solutions of aryllithium compounds in pure diethyl ether are not usually sufficiently stable on storage. For this reason, solutions of aryllithium compounds in ether-containing solvents having a restricted ether content have been developed. Aryllithium compounds decompose more slowly in these solutions. Thus U.S. Pat. No. 3,197,516 and U.S. Pat. No. 3,446,860 describe solutions of phenyllithium in diethyl ether/hydrocarbon mixtures. Such solutions have the disadvantages that they are only a moderate improvement as regards their heat stability and that they have to be stored in cold conditions (0° C. to 5° C.). Even at these temperatures a discoloration is to be observed after relatively prolonged storage, and phenyllithium/ether complexes frequently precipitate out in crystalline form.

Better, i.e. stabler, products can be obtained by using higher ethers. Thus WO 92/19622 describes a process for preparing solutions of aryllithium compounds in ethereal solvents ROR' where R, R', independently of one another, are alkyl groups having 3 to 8 C atoms. With the use of dibutyl ether, for example, 5% to 25% phenyllithium solutions which are stable for three weeks at 40° C. are obtained. Disadvantages of this process, however, are yields which reproduced and the inferior purity of the resulting products. An example giving a very high yield (96%) and extremely high product purity (>99%) is described in WO 92/19622, but these data could not be reproduced.

Thus, in U.S. Pat. No. 5,626,798 (the same applicant as the applicant of WO 92/19622) there is the criticism that product solutions in which dibutyl ether is used as solvent are in fact stabler, but that difficulties arose owing to the decreased Lewis basicity of the solvent employed. Thus the rate of the reaction between lithium metal and chlorobenzene decreased during the final quarter of the halide addition. Owing to this retarding of the reaction, impurities such as diphenyllithium and diphenyl were formed as a result of secondary reactions between phenyllithium and chlorobenzene. This led inevitably to a decrease in the phenyllithium content during storage. These observations could be confirmed in experiments by the present writers (see Comparison Example B).

In order to increase the reaction rate, U.S. Pat. No. 5,626,798 recommends the addition of certain Lewis bases corresponding to the formula $R^2AR^3(R^4)$ or of cyclic compounds $(CR^5R^6)_yA(R^4)_z$, wherein A is selected from oxygen, nitrogen, phosphorus or sulfur; $R^2$, $R^3$ and $R^4$ are selected from alkyl groups having 1 to 6 C atoms; $R^5$ and $R^6$ are independently selected from hydrogen or alkyl groups containing up to 6 C atoms; y is an integer between 0.4 and 6; if A is oxygen or sulfur, z is equal to zero and if A is nitrogen or phosphorus, z is equal to 1. Here the molar ratio of ether to aryl halide is at least 1.3 to 1 and the molar ratio of Lewis base to aryl halide is 0.01 to 0.50.

Disadvantages of this process are the still unsatisfactory yields of 87.4% to 91.5% (see the three examples described in U.S. Pat. No. 5,626,798), but above all the decreased stability on storage. U.S. Pat. No. 5,626,798 gives no details regarding this, but in comparison examples by the present writers it was shown that solutions which contain the required Lewis bases, in particular MTBE (methyl tert.butyl ether), decompose considerably more rapidly than do those without the above-mentioned additives (see the present Examples, Table 1). The cause of this is an attack of the aryllithium compounds on the Lewis bases, presumably accompanied by splitting of the C—O— bonds. In this way, black-coloured solutions having a distinctly increased residual base content are formed. Moreover, the product solutions prepared as in U.S. Pat. No. 5,626,798 still have a relatively high aryl halide content. Thus, the product described as Example 1 has a chlorobenzene content of 1 wt.% (corresponding to 3.3 mol.%), which is indeed reduced in comparison with prior art, but is still very high. The diphenyl content is also still unsatisfactorily high (see the present Comparison Example A, Table 3).

The object of the present invention is to avoid the disadvantages of the prior art and to demonstrate a process for the preparation of aryllithium compounds which avoids the slowing down of the rate of the reaction between aryl halide and lithium metal (in particular in the final quarter of the aryl halide addition) and delivers a pure product having a high yield (for example >90%). By product purity is meant in particular a decreased content of coupling products (for example, diphenyl), aryl halides and residual base (formation as a result of attack on Lewis bases having high Lewis basicity).

The object is achieved by a process for the preparation of aryllithium compounds, in which metallic lithium, which is preferably in the form of a dispersion, in an ether-containing solvent is reacted with an aryl halide and a catalyst is added prior to or at the beginning of the reaction, a catalyst is added, the catalyst containing a halogen-free, polynuclear aromatic (aryl catalyst) or consisting of such a compound.

Surprisingly, it has been found that halogen-free, polynuclear aromatics accelerate the reaction and at the same time improve the selectivity, i.e. under otherwise comparable reaction conditions, a product solution prepared according to the invention will be significantly purer than a product prepared according to prior art. In particular, the residual contents of aryl halide and Wurtz secondary products are decreased.

The aryl catalyst is added prior to the beginning or at the beginning of the reaction. In this connection, the definition of "at the beginning" is that the addition of the aryl catalyst is terminated when half the total quantity of the aryl halide to be introduced has been added to the reaction.

The aryl catalyst used may be a polynuclear, halogen-free aromatic selected from the group of ortho-condensed aromatics or from the group of aromatics bonded to one another by single bonds; the aromatic may be alkyl-substituted. Examples of such catalysts are given below:

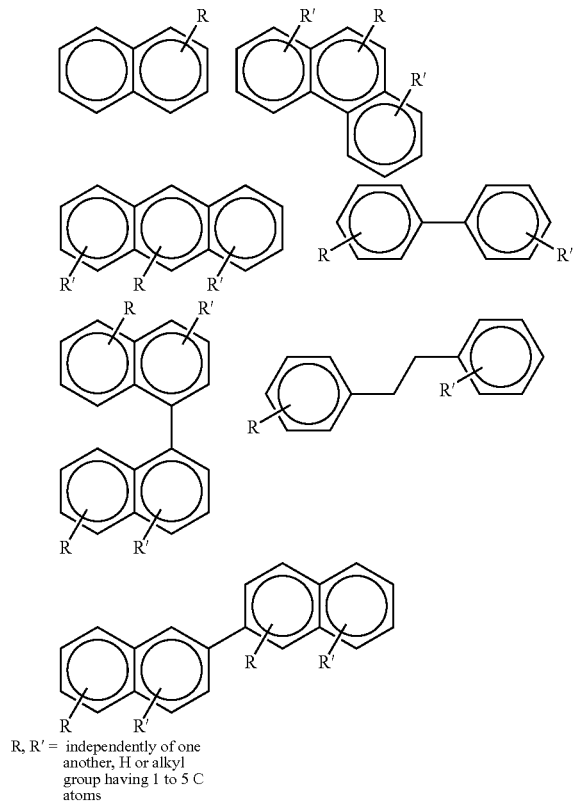

R, R' = independently of one another, H or alkyl group having 1 to 5 C atoms

Suitable aryl catalysts are, in particular, the Wurtz coupling products formed during the reaction. In this case the preparation process is clearly optimised, without the admixture of a foreign substance. In some cases, in particular if the given coupling product is not commercially available, it may be appropriate to use another aryl catalyst.

For example, ortho-condensed, polycyclic aromatics such as naphthalene, phenanthrene, anthracene et cetera, which may be singly or multiply alkyl-substituted, may be used. In addition, aromatic systems bonded by single bonds, such as diphenyl, 4,4'-di-tert.butyldiphenyl, dinaphthyl et cetera, may also be used.

The optimal quantity of aryl catalyst has to be tried out in individual cases. It is determined by the "activity" of the catalyst, i.e. especially by the rate of formation and stability of the radical anion formed with lithium metal and of the solvent/aryl halide combination. Thus, for example, in the preparation of phenyllithium solutions in aliphatic ethers R—O—R' where R, R' are alkyl groups having at least 3 C atoms, preferably 0.1 to 0.6 mol. % (based on the quantity of aryl halide used) of a binuclear aromatic bonded by a single bond, for example, diphenyl or 4,4'-di-tert.butyl diphenyl, is added. As a rule, the required quantity of catalyst is between 0.05 and 2 mol. %, based on the total quantity of aryl halide used in each case.

Preferably the metallic lithium is in finely divided form, with the particle sizes being preferably <0.1 mm and particularly preferably <0.05 mm. Preferably the lithium metal has an Na content of 0.5 to 5 wt. %, particularly preferably 1 to 3 wt. %. Preferably an excess of lithium to aryl halide is used.

The excess is preferably 1 to 40 mol. %, particularly preferably 5 to 25 mol. %.

The solvents used are ethers, either in pure form or in a mixture with hydrocarbons. The ethers may be acyclic or cyclic. Acyclic ethers R—O—R' where R and R', independently of one another, are $C_1$ to $C_6$ may also be used in a mixture or together with cyclic ethers (preferably having 4 to 8 C atoms). Preferred ethereal solvents are: diethyl ether, dipropyl ether, dibutyl ether, tert.butyl methyl ether (MTBE), tert.amyl methyl ether, tetrahydrofuran, 2-methyltetrahydrofuran and tetrahydropyran. Dibutyl ether and diethyl ether are most preferred.

Besides ethers, the ethereal solvent may also contain anhydrous hydrocarbons in a quantity of 50 wt. % at most, based on the total quantity of solvent. Suitable hydrocarbons are alkanes having 5 to 8 C atoms, for example, pentane, hexane, heptane, octane, cyclohexane or methylcyclohexane. In addition, liquid aromatics having up to 8 C atoms, for example, benzene, toluene, ethylbenzene and xylenes, may also be used. Cyclohexane, methylcyclohexane and toluene are particularly preferred.

The process according to the invention is generally suitable for the preparation of lithiated mononuclear or polynuclear aromatics or heteroaromatics. The respective aromatics may also carry 1 to 3 substitutents. Such substitutents may be selected, for example, from the following groups: alkyl (R having 1 to 10 C atoms), phenyl ($C_6H_5$—), tolyl ($C_7H_8$—), alkoxy (R—O— where R is an alkyl group having 1 to 10 C atoms), dialkylamino (RR'N, where R and R', independently of one another, are alkyl groups having 1 to 10 C atoms) and $F^-$ (fluorine).

Examples of mononuclear aryllithium compounds are: phenyllithium, 2-, 3- or 4-tolyllithium, cumyllithium, 4-dimethylaminophenyllithium, 2-lithioanisole, 2-, 3- or 4-fluorophenyllithium or fluorotoyllithium.

Examples of polynuclear aryllithium compounds are: α-naphthyllithium, β-naphthyllithium, anthracenyllithium or phenanthrenyllithium.

Examples of heteroaromatics are 2- and 3-thienyllithium and 2- and 3-furanyllithium.

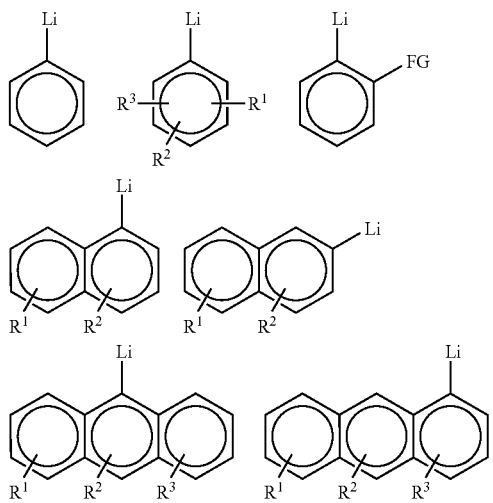

-continued

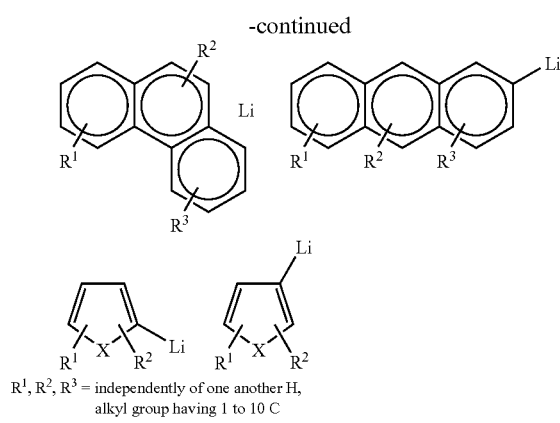

$R^1$, $R^2$, $R^3$ = independently of one another H, alkyl group having 1 to 10 C atoms, phenyl, toluene, F FG = functional groups such as $OR^1$, $NR^1R^2$ X = O, S, Te, $NR^1$ Aryl halides Ar-Hal wherein Hal=Cl, Br or I are used as starting compounds. The chlorine compounds (for example, chlorobenzene) are particularly preferred, as these are generally the most readily available and are cheap and form Wurtz secondary products the least. The commercially available halides do not usually require further preliminary treatment. Should they be contaminated with water or hydrogen halide (H-Hal), however, it is recommended that an ordinary purification step, for example, filtration through a molecular sieve, be carried out.

Preferably a drying agent, such as lithium hydride or final product solution, is added to the lithium metal suspension prior to the addition of the aryl halide. The addition of the aryl halide takes preferably 5 minutes to 5 hours, particularly preferably 30 to 180 minutes. The temperature of the reaction (addition stage and post-reaction stage) is preferably −20° C. to +100° C., particularly preferably 0° C. to 60° C.

The process according to the invention may be carried out, for example, as follows:—

The required anhydrous, aprotic solvent is placed in a dry reaction vessel which has been rendered inert (i.e. filled with protective gas such as argon or nitrogen) and finely-divided lithium metal is added thereto. The lithium metal is generally used in the form of powder, i.e. having particle sizes <0.1 mm, preferably <0.05 mm. In the case of certain solvent/product combinations, coarser lithium metal, for example, granular material having a diameter of approximately 1 to 3 mm, may also be used. It is particularly advantageous to use a quality of lithium having a relatively high sodium content of 0.5 to 5 wt. %, particularly preferably 1 to 3 wt. %. The quantity of lithium corresponds to at least the stoichiometric quantity, i.e. twice the molar quantity, of the subsequently added aryl halide. The lithium is preferably used in excess, i.e. in 1 to 40 mol. % excess, particularly preferably in 5 to 25 mol. % excess.

The halogen-free, polynuclear aryl catalyst is then added and stirred for 5 to 100 minutes at 0° C. to 60° C. In particular, if the raw materials used have been imperfectly pretreated, i.e. are not quite free of water and other protic contaminants, it is recommended that the reaction mixture be activated. To that end, a small quantity of a non-interfering drying agent (for example, lithium hydride in quantities of approximately 0.1 to 10 g/kg solvent) is added and stirred for a few minutes to several hours. Alternatively, final product solution from a previous batch (for example, 0.1 to 50 ml/kg solvent) may also be added. The Ar—Li contained in the product solution reacts with the interfering contaminants with the resulting formation of an "inert reaction mixture", which readily reacts with the aryl halide added in the following step. It is also particularly elegant to add at the "start" of a batch, or to introduce beforehand, a solution of the Ar—Li end product containing the aryl catalyst.

The reaction mixture, thus preconditioned, is now brought to the required reaction temperature which, depending on the solvent/halide combination, may be a temperature between −20° C. and 100° C., preferably 0° C. and 60° C. In the case where Ar is phenyl, the particularly preferred reaction temperature is between 20° C. and 45° C. The aryl halide may be introduced in pure form or dissolved, preferably in the same solvent as that already used for the preparation of the Li metal suspension. In the case of liquid aryl halides, it is preferable to use these undiluted.

The halide is added over a period typically of 5 minutes to 5 hours, preferably 30 to 180 minutes. In the course of this, the metal suspension is stirred vigorously. The start of the reaction between aryl halide and metal can be easily discerned from the rise in temperature (heat of reaction) and from the formation of the insoluble lithium halide secondary products. In order to maintain the required temperature, the reaction is countercooled from outside.

On conclusion of the addition, stirring is continued for at least as long as liberated heat of reaction is observed. This is generally the case for 10 minutes to 4 hours. On the laboratory scale, stirring is frequently carried out overnight. The finally reacted reaction suspension is then worked up in known manner, i.e. it is usually filtered. A solution of the respective aryllithium compound in an ether-containing solvent is obtained.

The halide content of the aryllithium compounds obtained, which is decreased as a result of the process according to the invention, leads to products which are more stable in storage, because the Wurtz secondary reaction corresponding to

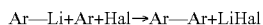

in the final product solution is greatly diminished or prevented. The formation of Wurtz secondary product also takes place during the product synthesis, the extent of the secondary reaction being dependent on the nature of the solvent, of the halide, of the temperature and also in particular on the quality (i.e. activity, specific surface) and quantity (stoichiometric quantity or excess) of the lithium used. Unexpectedly, as a result of the addition according to the invention of the catalysts, in particular of the Wurtz coupling product Ar—Ar which is inevitably formed in certain quantities, the total content of this secondary product observed at the end of the reaction can be greatly decreased, i.e. in the product solutions prepared according to the invention, the sum of externally added Wurtz product Ar—Ar and that which is formed as secondary product is lower than is the case of products prepared according to prior art.

The process according to the invention also has the advantage that good reaction yields and short reaction times can be achieved simultaneously, without the need for the presence of Lewis bases, which hitherto have been thought necessary. The product solutions containing no Lewis bases are generally more stable. This is seen in Table 1, which shows the decomposition rates of approximately 15% phenyllithium solutions in pure dibutyl ether and in a mixed solvent which contains, besides dibutyl ether, 7 mol.% methyl tert.butyl ether (MTBE, based on phenyllithium contained). To that end, the two solutions prepared by the process according to the invention were stored for eight weeks at 20° C. to 40° C. in tightly sealed glass vessels.

TABLE 1

Decomposition rates of phenyllithium in dibutyl ether (in % active base/day)

|  | at 20 C. | at 40 C. |
| --- | --- | --- |
| without MTBE | −0.019 | −0.079 |
| with 7 mol. % MTBE | −0.269 | −0.337 |

The solution containing added MTBE had moreover turned black, whereas the product containing exclusively dibutyl ether as solvent remained light brownish.

The invention is explained in more detail below by means of Examples.

EXAMPLE 1

Preparation of Phenyllithium in Dibutyl Ether, Catalyst 0.6 mol. % Diphenyl 11.5 g lithium powder (1657 mmol, particle size<0.1 mm, Na content=2.3 wt. %) and 0.17 g (19 mmol) finely ground lithium hydride in 160 g anhydrous dibutyl ether were placed in an inerted 500 ml double-jacketed glass reactor equipped with anchor stirrer, reflux condenser and internal thermometer and were heated to 32.5° C., with stirring. Then 0.67 g (4.3 mmol) diphenyl (>99%, Merck Schuchardt firm) was added and the whole was stirred for 10 minutes. A mixture of 77.5 g (688 mmol) chlorobenzene and 4.2 g (48 mmol) tert-.butyl methyl ether (MTBE) was added, dropwise, at an even rate over a period of 4 hours by means of a dosing device. The reaction started almost immediately; this was discernible from a rise in the internal temperature by 2° C. The internal temperature was maintained within the range of 32° C. and 35° C. by countercooling.

Immediately on conclusion of the addition, a sample was withdrawn and filtered clear by means of a spray filter. A conversion of 86% was ascertained by total base titration; a chlorobenzene content of 4 wt. % was detected by gas chromatography (GC).

After a two-hour post-reaction stage at approximately 32° C., no further heat of reaction was detectable. The reaction mixture was cooled to 20° C. and filtered through a fritted-glass filter and analysed:—

| Total base: | 3.009 mmol/g (corresponds to 97.4% conversion) |
| --- | --- |
| Residual base: | 0.25 mmol/g |
| Active base: | 2.759 mmol/g (corresponds to 23.2% phenyllithium) |

| GC analysis after hydrolysis: | |
| --- | --- |
| Diphenyl: | 0.8 wt. % |
| Chlorobenzene: | 0.4 wt. % |
| Benzene: | 23.2 wt. % |
| MTBE: | 1.8 wt. % |
| Dibutyl ether: | 72.6 wt. % |

The diphenyl content of 0.8 wt. % corresponds to a content of 2.0 mol. % based on phenyllithium.

EXAMPLES 2 to 9 AND COMPARATIVE EXAMPLES A TO D

Preparation of Aryllithium Compounds (Ar—Li) in Ethereal Solvents, with and without Catalyst Further examples of the reaction were carried out in a laboratory calorimeter under varied reaction conditions. This organisation of the experiments allows the precise observation of the liberated heat of reaction and hence, indirectly, the determination of the reaction rate and of the so-called "thermal degree of conversion". The thermal degree of conversion, a dimensionless number, is found by division of the heat liberated up to a given time by the total (on complete conversion) heat liberated. It thus corresponds to the progress of the respective reaction.

The further Examples 2 to 9 according to the invention were carried out similarly to Example 1, and the individual variables may be found in Table 2. The Comparison Examples A to D corresponding to prior art were carried out under otherwise identical reaction conditions, without the addition of a catalyst. The individual variables may be found in Table 2. All the Examples reported in Table 2 were carried out, like Example 1, using a 20 mol. % excess of lithium.

TABLE 2

Examples 2 to 9, Comparison Examples A to D, Preparation of aryllithium compounds (Ar—Li) in ethereal solvents

| Ex. | Ar—Li[1] | Dosing time | Post-reaction time | React. temp. | MTBE[2] | Solvent[3] | Catalyst[4] | thermal degree of conversion at end of dosing | Conversion End of dosing | Conversion filtrate | Yield (incl. washing) (%) |
| --- | --- | --- | --- | --- | --- | --- | --- | --- | --- | --- | --- |
| 2 | Ph | 1 | 3 | 32-38 | 7 | BU$_2$O | 0.6 DP | 82 | n.d. | 97.2 | 95.1 |
| A | Ph | 1 | 4 | 32-38 | 7 | BU$_2$O | ./. | 65 | n.d. | 89.6 | 85.0 |
| 3 | Ph | 1 | 2 | 32-38 | ./. | BU$_2$O | 0.3 DP | 83 | 72.9 | 97.0 | 94.0 |
| B | Ph | 1 | 4 | 32-38 | ./. | BU$_2$O | ./. | 73 | 63.0 | 91.3 | 90.8 |
| 4 | Ph | 1 | 3.5 | 32-38 | ./. | BU$_2$O | 0.1 N | 72 | 65.9 | 95.6 | 92.5 |
| 5 | Ph | 1 | 4 | 32-38 | ./. | BU$_2$O | 0.3 TBDP | 69.7 | 61.5 | 93.4 | 92.3 |
| 6 | Ph | 2 | 3 | 20-23 | ./. | Et$_2$O/CH | 0.1 DP | 85.6 | 76.8 | 98.0 | 95.4 |
| 7 | Ph | 2 | 3 | 20-23 | ./. | Et$_2$O/CH | 0.3 DP | 88 | 80.7 | 93.6 | 88 |
| 8 | Ph | 2 | 3 | 20-23 | ./. | Et$_2$O/CH | 0.5 DP | 89 | 80 | 97.3 | 92.9 |
| C | Ph | 2 | 4 | 20-23 | ./. | Et$_2$O/CH | ./. | 82.6 | 57.9 | 84.1 | 79.5 |

TABLE 2-continued

Examples 2 to 9, Comparison Examples A to D, Preparation of aryllithium compounds (Ar—Li) in ethereal solvents

| Ex. | Ar—Li[1] | Dosing time | Post-reaction time | React. temp. | MTBE[2] | Solvent[3] | Catalyst[4] | thermal degree of conversion at end of dosing | Conversion End of dosing | Conversion filtrate | Yield (incl. washing) (%) |
|---|---|---|---|---|---|---|---|---|---|---|---|
| 9 | p-Tol | 2 | 2.5 | 20-23 | ./. | Bu$_2$O | 0.3 DP | 84.4 | 78.6 | 95.2 | 93.2 |
| D | p-Tol | 2 | 2.5 | 20-23 | ./. | Bu$_2$O | ./. | 86.9 | 75.0 | 94.8 | 89.6 |

[1]Ph = phenyl
p-Tol = p-tolyl
[2]MTBE = tert butyl methyl ether
[3]BU$_2$O = dibutyl ether
Et$_2$O/CH = mixture of 35% diethyl ether, 65% cyclohexane
[4]DP = diphenyl
N = naphthalene
TBDP = di-tert·butyldiphenyl
n.d. = not determined The reaction-accelerating and yield-enhancing effect of the addition according to the invention of the aryl catalysts may be inferred from Examples 2 to 9 and the corresponding Comparative Examples A to D.

Example 2 and Comparative Example A describe the synthesis of phenyllithium in a mixture of dibutyl ether with 7 mol. % MTBE at a reaction temperature of between 32° C. and 38° C. At the end of the dosing time, 1 hour in each case, in the Example according to the invention 82% of the total heat of reaction had already been liberated, whereas without a catalyst only 65% of the heat was released. The yield in Example 2 is approximately 99%, which is almost 10% more than in Comparative Example A.

Similar effects also occur at half the catalyst concentration and in the absence of the Lewis base MTBE (Example 3 and Comparative Example B).

Example 4 demonstrates that naphthalene also, even at a very low concentration of 0.1 mol. %, brings about a rise in conversion and in yield of approximately 3% more than in Comparative Example B.

The addition according to the invention of the catalyst di-tert.butyldiphenyl does not lead to an acceleration of the reaction, but to an increase in conversion and in yield (Example 5 compared with Comparative Example B).

Examples 6 to 8 and Comparative Example C show that in a mixed solvent consisting of 35 parts by weight diethyl ether and 65% cyclohexane, the addition according to the invention of the aryl catalyst diphenyl likewise has a positive effect: yields and conversions are significantly improved relative to those in Comparative Example C. Particularly striking, too, is the considerably higher reaction rate, which can be deduced from the different conversions at the time of the added reagent.

Example 9 and Comparative Example D show the preparation of p-tolyllithium in dibutyl ether. For a relatively long dosing time of two hours, in Example 9 the thermal conversion at the end of dosing is somewhat less than in Comparative Example D, but the conversions and the product yield are significantly higher in the Example according to the invention.

Samples of the clear-filtered end products obtained from the Examples and Comparative Examples listed in Table 2 were withdrawn and their compositions analysed by gas chromatography. The results are shown in Table 3.

TABLE 3

Compositions of the clear-filtered products from Table 2

| Example | Chlorobenzene (wt. %) | Diphenyl (wt. %) | Phenyllithium (wt. %) | Diphenyl (mol. %)* |
|---|---|---|---|---|
| 2 | 0.24 | 0.93 | 25.1 | 2.0 |
| A | 1.6 | 2.9 | 21.2 | 6.9 |
| 3 | 0.4 | 0.8 | 24.0 | 2.2 |
| B | 1.3 | 1.1 | 23.4 | 3.1 |
| 6 | 0.6 | 0.9 | 23.9 | 2.4 |
| 7 | 0.2 | 0.5 | 22.8 | 1.4 |
| 8 | 0.9 | 0.8 | 23.7 | 2.2 |
| C | 4.5 | 0.9 | 20.9 | 2.8 |

*based on phenyllithium

It can be seen from Table 3 that the products prepared by the process according to the invention have a higher purity than do the products prepared according to prior art and are obtained in higher yield. Thus, for example, a decrease of 85% in the chlorobenzene content and of 70% in the diphenyl content is established from a comparison of Example 2 and Comparative Example A.

The invention claimed is:

1. A process for the preparation of an aryllithium compound comprising reacting lithium metal in finely divided form having a particle size of less than 0.1 mm with an aryl halide in a solvent comprising an ether, and adding an aryl catalyst, said aryl catalyst comprising a halogen-free, polynuclear aromatic compound, prior to or at the beginning of the reaction to produce the aryllithium compound, wherein the lithium metal is in excess based on the total mount of aryl halide and wherein the aryl catalyst is added in a quantity of 0.05 to 2 mol. % based on the total mount of aryl halide and wherein an excess of 1 to 40 mol. % lithium is present based on the total mount of aryl halide.

2. A process according to claim 1, wherein the aryl catalyst is selected from the group consisting of ortho-condensed aromatics and aromatics bonded to one another by single bond.

3. A process according to claim 2, wherein said aryl catalyst is selected from the group consisting of naphthalene, phenanthrene, anthracene, diphenyl and 4,4'-di-tert-butyl-diphenyl.

4. A process according to claim 2, wherein the lithium metal has a sodium content of 0.5 to 5 wt. %.

5. A process according to claim 1, wherein the lithium metal has a sodium content of 0.5 to 5 wt. %.

6. A process according to claim 1, wherein said ether is at least one ether selected from the group consisting of an acyclic ether of formula R—O—R' wherein R and R' independently comprise 1 to 6 carbon atoms and a cyclic ether comprising 4 to 8 carbon atoms.

7. A process according to claim 1, wherein the ether containing solvent comprises at least one of diethyl ether, dipropyl ether, dibutyl ether, tertiary butyl methyl ether, tertiary amyl methyl ether, tetrahydrofuran, 2-methyltetrahydrofuran or tetrahydropyran.

8. A process according to claim 1, wherein the ether containing solvent further comprises an anhydrous hydrocarbon in a quantity of up to 50 wt. % based on the total quantity of solvent.

9. A process according to claim 1, wherein a drying agent is added to the lithium metal suspension prior to the addition of the aryl halide.

10. A process according to claim 7, wherein the temperature of the reaction during the addition stage and post-reaction stage is −20° C. to +100° C.

11. A process according to claim 1, wherein the aryl halide used is a halobenzene and the ether-containing solvent used is dibutyl ether and that phenyllithium is obtained as product.

12. A process according to claim 1, wherein the ether containing solvent contains another ether in addition to dibutyl ether.

13. A process according to claim 1, wherein that the aryl halide used is a halobenzene and the ether-containing solvent used is dibutyl ether in a mixture with cyclohexane.

14. A process according to claim 1, wherein lithium metal has a particle size of less than 0.05 mm.

15. A process for the preparation of an aryllithium compound comprising reacting lithium metal having a particle size of approximately 1 to 3 mm in a solvent comprising an ether with an aryl halide, and adding an aryl catalyst comprising a halogen-free, polynuclear aromatic compound prior to or at the beginning of the reaction to produce the aryllithium compound, wherein the lithium metal is in excess based on the total mount of aryl halide and wherein the aryl catalyst is added in a quantity of 0.05 to 2 mol. % based on the total mount of aryl halide and wherein an excess of 1 to 40 mol. % lithium is present based on the total mount of aryl halide.

16. A process according to claim 15, wherein said lithium has a sodium content of from 0.5 to 5 wt. %.

17. A process for the preparation of an aryllithium compound comprising reacting lithium metal in finely divided form having a particle size of less than 0.1 mm with an aryl halide in a solvent comprising an ether, and adding an aryl catalyst comprising a halogen-free, polynuclear aromatic compound at the beginning of the reaction such that addition of the aryl catalyst is terminated when half of the total amount of aryl halide has been added to produce the aryllithium compound, wherein the lithium metal is in excess based on the total mount of aryl halide and wherein the aryl catalyst is added in a quantity of 0.05 to 2 mol. % based on the total mount of aryl halide and wherein an excess of 1 to 40 mol. % lithium is present based on the total mount of aryl halide.

18. A process for the preparation of an aryllithium compound comprising reacting into a single reactor lithium metal in powder form with an aryl halide in a solvent comprising an ether, and adding an aryl catalyst that is a halogen-free, polynuclear aromatic compound prior to or at the beginning of the reaction to react with the lithium to produce the aryllithium compound, wherein the lithium metal is in excess based on the total mount of aryl halide and wherein the aryl catalyst is added in a quantity of 0.05 to 2 mol. % based on the total mount of aryl halide and wherein an excess of 1 to 40 mol. % lithium is present based on the total mount of aryl halide.

* * * * *